US005766902A

United States Patent [19]

Craig et al.

[11] Patent Number: 5,766,902

[45] Date of Patent: Jun. 16, 1998

[54] TRANSFECTION PROCESS

[75] Inventors: Roger Kingdon Craig, Smallwood; Mike Antoniou, Edgeware; Hakim Djeha, West Didbury, all of United Kingdom

[73] Assignee: Therexsys Limited, London, United Kingdom

[21] Appl. No.: 487,473

[22] Filed: Jun. 7, 1995

Related U.S. Application Data

[63] Continuation-in-part of PCT/IB94/01835, Aug. 22, 1994.

[30] Foreign Application Priority Data

Aug. 20, 1993 [GB] United Kingdom ............... 9317380

[51] Int. Cl.$^6$ .................... C12N 15/00; C12N 13/00
[52] U.S. Cl. .................... 435/172.3; 435/173.5
[58] Field of Search .................... 514/44; 435/2, 435/240, 172.3, 173.5; 424/450; 935/52, 62; 530/391.7

[56] References Cited

U.S. PATENT DOCUMENTS

| | | | |
|---|---|---|---|
| 4,923,437 | 5/1990 | Gordon | 600/12 |
| 5,436,151 | 7/1995 | McGlave et al. | 435/373 |
| 5,521,291 | 5/1996 | Curiel et al. | 530/391.7 |

FOREIGN PATENT DOCUMENTS

WO93/04701  3/1993  WIPO .................... C12N 15/87

OTHER PUBLICATIONS

Barinaga, M. 1994 Science vol. 266, p. 1326.
Marshall, E. 1995 Science vol. pp. 1050–1055.
Crystal, R. 1995 Science vol. 270 pp. 404–410.
Jolly D. 1994 Cancer Gene Therapy vol. 1(1) pp. 51–64.
Orkin, S.H. Dec. 1995 Report Recommendations of the Panel to Assess the NIH Investment in Research on Gene Therapy.

Wilson et al., "Evaluation of the interjection method for introducing proteins into living cells," *Am. J. Phys.*, vol. 260, pp. C355–C363, (1991).

Croaker et al., "Electric Field–Mediated Gene Transfer into K562 Cells: Optimization of Parameters Affecting Efficiency," *Leukemia*, vol. 4, No. 7, pp. 502–507, (1990).

Bergan et al., "Electroporation enhances c-myc antisense oligodeoxynuceotide efficiency," *Nucleic Acids Research*, vol. 21, No. 15, pp. 3567–3573, (1993).

Citro et al., "Inhibition of Leukemia cell proliferation by receptor–mediated uptake of c–myb antisense oligodeoxynucleotides," *Proc. Natl. Acad. Sci. USA*, vol. 89, pp. 7031–7035, (1992).

Wagner et al., "Influenza virus hemagglutinin HA–2 N–terminal fusogenic peptides augment gene transfer by transferrin–polylysine–DNA copmlexes: Toward a synthetic virus–like gene –transfer vehicle," *Proc. Natl. Acad. Sci. USA*, vol. 89, pp. 7934–7938, (1992).

Machy et al., "Gene transfer from targeted liposomes to specific lymphoid cells by electroporation," *Proc. Natl. Acad. Sci. USA*, vol. 85, pp. 8027–8031, (1988).

International Search Report for Corresponding PCT application, listing references identified in search.

Curiel et al., "Adenovirus enhancement of transferrin–polylysine–mediated gene delivery," *Proc. Natl. Acad. Sci. USA*, vol. 88, pp. 8850–8854, (1991).

*Primary Examiner*—James Ketter
*Assistant Examiner*—Irem Yucel
*Attorney, Agent, or Firm*—Banner & Witcoff, Ltd.

[57] ABSTRACT

A method for delivering to a target cell in a population of cells a biologically active agent comprising the steps of exposing the population of cells to a complex comprising the biologically active agent and a ligand capable of binding to the target cell and subjecting the population of cells to an electric field while maintaining cell viability.

19 Claims, 9 Drawing Sheets

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO: 1:

```
Gly Leu Phe Gly Ala Ile Ala Gly Phe Ile Gly Ala Gly Thr Gly Gly
 1               5                  10                  15

Met Ile Ala Gly Gly Gly Cys
                20
```

TRANSFECTION PROCESS

This application is a continuation in part of PCT/IB94/01835, filed Aug. 22, 1994.

The present invention relates to a process for the transfection of cells with targeted nucleic acid vectors.

BACKGROUND

The uptake of nucleic acid vectors by cells is central to molecular biology and the application of molecular biology to clinical contexts. Since the introduction of DEAE and calcium phosphate mediated transfection techniques, it has been sought to improve the efficiency of transfection processes. This has given rise to a large number of protocols for delivering nucleic acid to cells, including techniques such as liposome delivery, microinjection and lipofection. One such improved technique is electroporation (see Tsong, 1991). In addition to the introduction of DNA, electroporation has also been used for the introduction of a variety of macromolecules including enzymes, antibodies and cell membrane proteins into isolated cells or tissues in vivo (see Weaver, 1993).

Electroporation of cells involves the application of a voltage across the cell membrane, which causes the formation of pores therein and an increase in its conductance for a short period of time, on the order of microseconds or milliseconds, so permitting the uptake of macromolecules and other substances by candidate mechanisms such as electrical drift, electrosmosis or diffusion.

Whilst the precise mechanism remains to be established, it is known that the mechanism is reversible and target cells such as erythrocytes remain visible after stable insertion of membrane proteins (Mouneimne et al., 1989). Unfortunately, electroporation using the large electric fields necessary for the introduction of nucleic acids is also associated with a high incidence of cell stress and death. The use of such large electric fields, whilst increasing the number of cells as a percentage of the starting population which take up DNA, also leads to a simultaneous decrease in the percentage of surviving cells. Therefore, the efficiency of electroporation is limited by the tendency to kill cells at the field strengths which are required to give a high transfection efficiency.

Although the general transfection techniques alluded to above, including electroporation, are effective in certain conditions, they remain ineffective when it is desired to selectively target a particular cell type in a heterogenous population of cells. This is due to the absence of any selective event in the general transfection processes. The available nucleic acid is taken up by all cells, although the efficiency of DNA uptake may vary from cell type to cell type.

Targeted uptake has been explored by a number of laboratories. One of the first effective targeted transfection techniques was disclosed by Wu (Wu and Wu, 1987; Wu et al., 1989). This technique, receptor-mediated gene transfer, targeted a DNA vector to hepatocytes by complexing the vector to a glycoprotein, which is bound by asialoglycoprotein receptors on hepatocytes. Effective targeting of vectors to hepatocytes was demonstrated in vivo and in vitro.

Receptor-mediated gene transfer is dependent upon the presence of suitable ligands on the surfaces of cells which will allow specific targeting to the desired cell type followed by internalisation of the complex and expression of the DNA. This can give rise to a number of problems, since cell-surface markers are often shared between cell types.

Solutions to this problem have been proposed (see inter alia, UK patent application No. 9325759.0) but, to date, the most usually cited solution is to purify the cells to be transfected, treat them and subsequently re-introduce them into the original cell population.

One solution which has been proposed which avoids the requirement to separate the target cell involves the conjugation of the vector, or delivery system, to antibodies, which can be designed to target highly specific cell-surface antigens (Wong and Huang, 1987; Roux et al., 1989; Trubetskoy et al., 1992; Hirsch et al., 1993). As in the method of Wu, nucleic acid may be attached to antibody molecules using polylysine (Wagner et al., 1990; 1991).

Although the use of antibodies for vector targeting has been suggested and indeed described, the efficiency of vector uptake and expression by cells remains low (see WO 8805077, WO 9001951 and WO 9117773) and has been documented only in cell lines in culture, as opposed to human primary cells and tissues.

Increased expression of DNA derived from ligand-DNA complexes taken up by cells via an endosomal route has been achieved through the inclusion of endosomal disruption agents, such as influenza virus heamagglutinin fusogenic peptides, either in the targeting complex or in the medium immediately surrounding the target cell. However, since the mechanism of action of such peptides and their derivatives is known to be intracellular at the level of the endosome (Wiley and Skehel, 1987), their function is dependent on the presence of the entrapment of the DNA within a cellular endosome together with the peptide. Consequently, although fusogenic peptides can improve the efficiency of expression of DNA already internalised by the cell and entrapped within endosomes, the use of fusogenic peptides fails to address the issue of the efficiency of uptake into the endosomal compartment of DNA-ligand complexes bound to cell surface receptors, and hence the proportion of cells within a given cell population with are effectively transfected whilst retaining viability.

One object of the invention is to provide an improved transfection protocol which allows targeted delivery and uptake of nucleic acid vectors to specific cells at high efficiency, preferably in the absence of purification of the cells from mixed cell populations.

Another object of the invention is to provide a targeted delivery system which is sufficiently specific to allow targeting of the vector to a specific cell type, yet also sufficiently efficient to ensure that a substantial proportion of the targeted cells is transfected whilst maintaining cell viability. We now describe an improved method for the delivery of biologically active agents to cells which is of great clinical benefit.

SUMMARY OF THE INVENTION

The invention is based on the discovery that the efficiency of receptor mediated DNA uptake is enhanced by subjecting the cells to be transfected to a mild electric field in the presence of a cellular targeting complex. The invention encompasses an improved process for transfecting haemoaopoietic cells, especially stem cells and T-cells present in complex cell populations, with vectors targeted to specific cell-surface ligands.

According to the present invention, therefore, there is provided a method for delivering to a target cell in a population of cells a biologically active agent comprising the steps of:

a) exposing the population of cells to a complex comprising the agent and a ligand capable of binding to the target cell; and b) subjecting the population of cells to an electric field.

Preferably, the complex further comprises an endosomal disruption agent. Advantageously, the endosomal disruption agent is of viral origin, such as an influenza virus haemagglutinin fusogenic peptide or an analogue thereof.

It has been found that the combination of endosomal disruption agents (see Wiley and Skehel, 1987; White, 1990) and the method of the invention can result in a synergistic benefit, greatly increasing the effect of biological agents alone within host cells. It is believed, although the Applicants do not wish to limited by this theory, that the synergy is due to the operation of the method of the invention and the endosomal disruption agents at two different points in the agent internalisation process. The application of an electric field is believed to increase the internalisation of agents bound to the cell membrane via an endosomal route. The use of the endosomal disruption agent then increases the efficiency of the release of the agent from the endosome.

An advantage of the method of the invention is that unlike electroporation, which is not believed to act via an endosomal route, the viability of the target cells is maintained.

The method of the invention is suitable for targeting any cell type using an appropriate ligand, whether in a purified or heterogenous population, and displays improved efficiency of transfection and cell viability over the methods of the prior art. Accordingly, by "population of cells", it is intended to refer to purified populations consisting of a single cell type, including a single cell in isolation, as well as heterogenous populations comprising a plurality of cell types.

Preferably, the invention is applicable to unpurified, heterogenous populations comprising a plurality of cell types, where the targeting function of the complex may be exploited to selectively target a particular cell type in the heterogenous population.

At the same time, it is possible to exploit the invention to transform more than one cell type in a mixed population of cells, by using a ligand which is specific for a common receptor.

The improved transfection described herein is of immense value for therapeutic purposes, for example, for the therapeutically effective delivery of nucleic acid vectors to cells of the hematopoietic lineage (see FIG. 1), such as T-cells, B-cells or macrophages within a population of blood cells, or preferably to the hematopoietic stem cell itself, the progenitor of all cells within the lineage.

Preferably, the target cell is a hematopoietic cell present in a purified or unpurified population of cells. Preferably, the population of cells is obtained from blood. It is an advantage of the invention that purification of the target cell from blood before treatment is not essential. Preferably, the hematopoietic target cell is a stem cell, T cell, B cell or macrophage.

The biologically active agent of the invention may be any agent capable of eliciting a biological effect in a cell. Such agents may be proteins, nucleic acids, ions or other biologically active molecules.

Preferably, the biologically active agent is a nucleic acid comprising at least one transcription unit encoding a proteinaceous or RNA molecule capable of eliciting a biological effect.

Preferably, the transcription unit encodes a protein. For example, a growth factor, hormone, cytokine, a transcription factor, a cell surface protein or a structural protein of any kind. The protein may contain one or more domains of known function, not necessarily of mammalian origin. The protein may be homologous to the target cell or deficient, absent or mutated therein. For example, the transcription unit may encode a protein effective in the therapy of an infectious disease, for example in HIV therapy. Alternatively, the transcription unit may encode a protein capable of correcting a genetic defect or a protein deficiency.

In HIV therapy, the protein may be a non-specific toxin or an anti-viral agent whose expression or activity has been modified for anti-HIV use, for example by using an HIV-specific transactivation system to express the protein. Alternatively, the agent may be specifically designed as an anti-HIV agent. For example, a decoy gene, encoding trans-dominant negative mutants of HIV peptides such as the tat, nef, vpu, vpr or rev gene products, which have been modified such that their activating properties are abolished but they retain the ability to compete with the natural virus-encoded protein.

For the correction of a genetic defect or a protein deficiency, such a protein may be a lysosomal enzyme for the correction of Gaucher's or Auber's disease (Scott et al., 1990; Sorga et al., 1987), the $\alpha$ or $\beta$ globin gene for the correction of sickle cell anemia or thalassaemia, or calcitonin or oil antitrypsin to prevent the onset or progression of osteoporosis or emphysema.

Furthermore, it is envisaged that the product of the transcription unit may be an RNA molecule, such as an antisense RNA molecule (Mirabelli et al., 1991) or a ribozyme tailored to act in a specific manner (Cech et al., 1992).

In the present invention, a "ligand" is any entity capable of specific binding to the surface of a cell.

For example, any molecule for which a cellular receptor exists could be used as a ligand. Such substances comprise proteins, nucleic acids, carbohydrates and metal ions, optionally complexed with proteins. The use of altered ligand molecules having engineered specificities, including a plurality of specificities, is envisaged. Especially preferred are growth factors and antibodies and antigen-binding fragments thereof, such as Fab, (Fab$^1$)$_2$ and Fv fragments. The ability of each ligand or fragment thereof to deliver a biological agent must be determined on a case by case basis. Efficiency will vary dependent on parameters such as receptor density on cells and the affinity of ligands for cell surface eiptopes, as well as the precise mechanism of cell internalisation.

It should be emphasized that, in the present invention, the application of an electric field to the cells to be transfected is not equivalent to electroporation.

Unlike electroporation cell viability is maintained. The electric field applied would appear to enhance endosomal uptake, a cellular phenomenon, as opposed to electroporation which results in the production of physical pores in the cell membrane through which bodies may pass as a result of electrical drift, electrosmosis or diffusion, the proposed mechanisms for the introduction of material using electroporation (Weaver, 1993). Furthermore, the present invention provides a selective approach for the delivery of substances to target cells within heterogenous cell populations as opposed to the indiscriminate delivery of substances using electroporation.

Preferably, the electric field used in the method of the invention, over an electrode gap of 0.4 cm, operates at a capacitance of less than 600 µF, advantageously less than 500 µF. Most preferably, the capacitance lies between 200 and 300 µF and is optimally 250 µF. The voltage of the electric field is less critical to the operation of the invention, but is advantageously less than 400v and preferably between 200 and 350v.

Viability of between 60 and 100% has been obtained with the method of the invention. In contrast, standard conditions for electroportion of peripheral blood lymphocytes are 250v at 960 μF, with expected viability of abut 10 to 15% (see Bio-Rad GENE PULSER® Electroprotocol for Human Primary Lymphocytes).

The method of the invention may be used in vivo (Powell et al., 1989; Titomirov et al., 1991) as well as in vitro. In vitro use is especially indicated for ex vivo targeted delivery of DNA to hematopoietic stem cells present in bone marrow aspirate, peripheral blood or cord blood. Transfected cells may then be returned to the patient. The avoidance of a separate cell separation step is advantageous, as handling of cells inevitably carries the risk of infection and reduced cell viability, additional patient trauma and increased healthcare costs.

According to a second aspect fo the present invention, there is provided the use of a complex comprising a biologically active agent and a ligand in the preparation of a transfection mixture for use in the electrically stimulated delivery of the biologically active agent to a target cell to which the ligand is capable of binding.

Further features and advantages of the invention will become more fully apparent in the following description of the embodiments and drawings thereof and from the appended claims.

BRIEF DESCRIPTION OF THE DRAWINGS

The drawing will be briefly described.

DETAILED DESCRIPTION OF THE INVENTION

Figure 1:
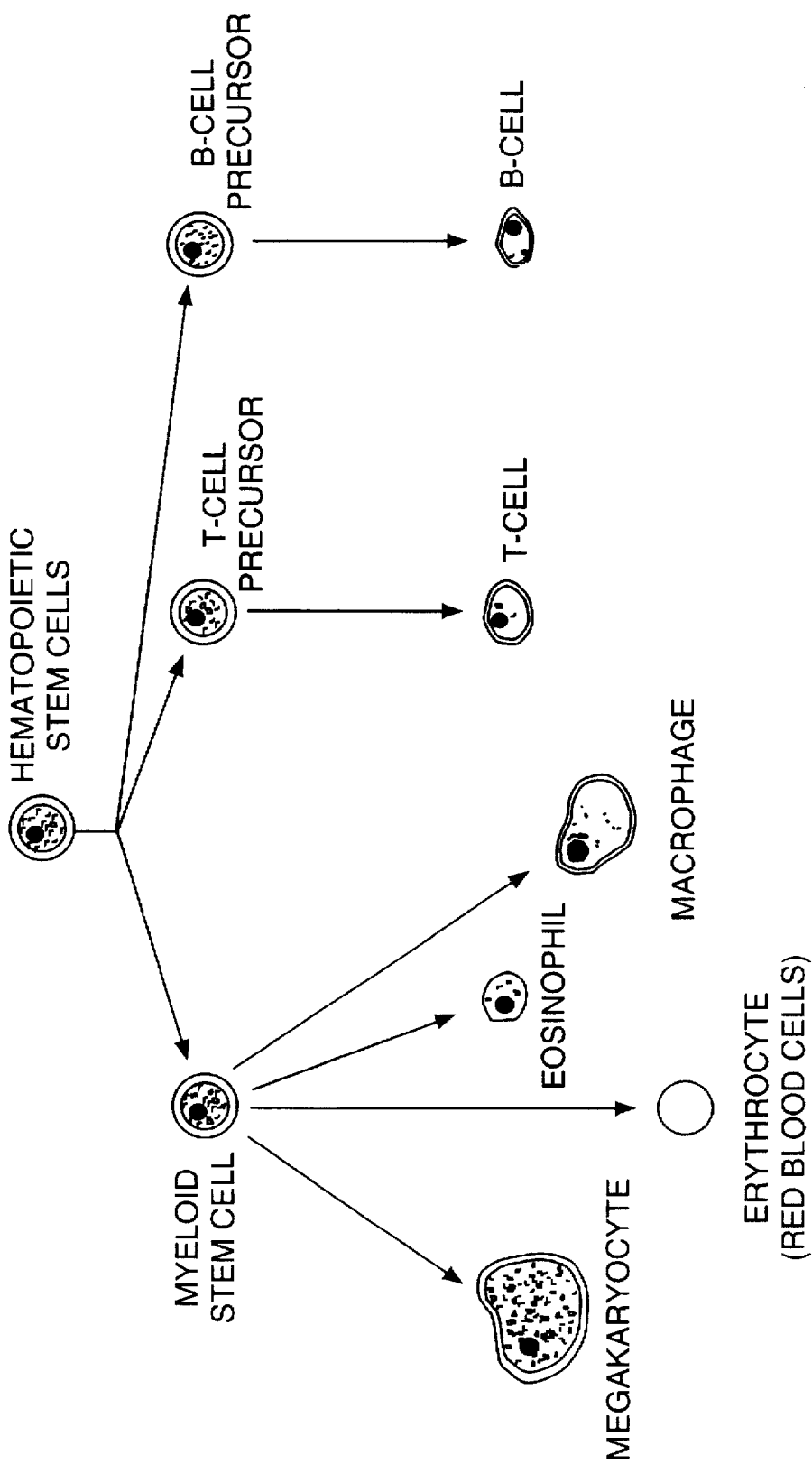
FIG. 1 is a schematic diagram showing the relationship of cells within the hematopoietic cell lineage.

The invention is illustrated by the following nonlimiting examples wherein the following materials and methods are employed. The entire disclosure of each of the literature references cited hereinafter are incorporated by reference herein.

The invention is based on the discovery that the efficiency of delivery of a biological agent to a target cell is greatly increased by subjecting the cell to a mild electric field in the presence of a cellular targeting complex.

The method of the invention encompasses the steps of (a) exposing a population of cells to a complex comprising a biologically active agent and a ligand capable of binding to a target cell in the cell population; and (b) subjecting the population of cells to an electric field.

The invention is broadly applicable to any cell targeting complex which interacts with the cell via a ligand-receptor interaction, that is, where the complex binds specifically to the cell and is internalized via an endosomal route. One complex which is particularly useful is a complex including an endosomal disruption agent which, when combined with the method of the invention, as described herein, produces synergistic benefit with respect to increasing the effect of the biological agent within the target cell.

The invention is most advantageously used with the following procedures. Example 1 below describes how the cells are subject to an electric field. Example 2 generally describes cellular targeting complexes useful in the invention. Example 3 describes preparation of antibody-polylysine-DNA complexes useful in the invention. Example 4 describes representative vectors useful in the invention. Example 5 describes application of the invention to introducing a recombinant DNA into human primary T-cells; Example 6 to CEM cells; Examples 7–9 to a mixture of blood cells containing T-cells; and Examples 10 and 11 to stem cells in a total white blood cell population. In Examples 5–11, a recombinant DNA vector containing a reporter gene was introduced into cells, and the reporter gene product detected. The reporter gene, of course, is representative of any gene encoding a biologically active agent.

The invention contemplates introduction into cells of a recombinant DNA useful in gene therapy or to treat a viral disease. The recombinant DNA will therefor contain a gene whose presence corrects a genetic defect in the host cell or organism or which combats a viral infection. Example 12 provides representative genes useful in gene therapy or in anti-viral therapy, and the corresponding diseases which the representative genes are used to treat.

EXAMPLE 1

Conditions for Subjecting Cells to an Electric Field According to the Invention After exposing the cells to the targeting complex, the cells are subject to an electric field according to the invention as follows. The cells are resuspended in electroporation-type buffer, for examples, Hepes buffer described hereinbelow, preferably by swirling rather than pipeting to avoid cell fragmentation, and transferred into an inter-electrode sterile electroporation cuvette. The cuvette is kept on ice for several minutes. Before electric shock treatment, the outside surface of the cuvettes is dried thoroughly to avoid a short circuit. The conditions to set up an electric field over a 0.4 cm electrode gap are as follows. The elecrtric field should operate at a capacitance of less than 600 uF, and preferably less than 500 uF. Most preferably, the capacitance will be betweeen 200 and 300 uF, and most optimally 250 uF. The voltage of the electric field is less critical than the capacitance, and will usually be less than 400 V, preferably between 200 and 350 V. For example, a single voltage pulse is applied at the conditions of 300 V and 250 uF capacitance using a Gene-Pulsar system (Bio-Rad). After electric shock, the cells are cooled on ice for several minutes, then removed into a fresh tube. The cells are then diluted, collected by low speed centrifugation, and resuspended in an appropriate medium.

EXAMPLE 2

Complexes Comprising a Biologically Active Agent and a Cell-Specific Ligand According to the Invention The invention contemplates transfer of a complex comprising a biological agent to a cell. Such transfer can be accomplished utilizing any ligand which is capable of specific binding to the surface of a cell, for example, as in receptor-mediated gene transfer.

Receptor-mediated gene transfer is dependent upon the presence of suitable ligands on the surfaces of cells which will allow specific targeting to the desired cell type followed by internalization of the complex and expression of the DNA. One form of receptor-mediated gene transfer is wherein a DNA vector is conjugated to antibodies which target with a high degree of specificity cell-surface antigens (Wong and Huang, 1987, Proc. Nat. Aca. Sci. 84:7851; Roux et al., 1989, Proc. Nat. Aca. Sci. 86:9079; Trubetskoy et al., 1992, Bioconjugate Chem. 3:323; and Hirsch et al., 1993, Transplant Proceedings 25:138). Nucleic acid may be attached to antibody molecules using polylysine (Wagner et al., 1990, Proc. Nat. Aca. Sci. 87:3410; Wagner et al., 1991, Proc. Nat. Aca. Sci. 89:7934) or via liposomes, as described below.

Thus, targeted gene delivery may be achieved according to the invention using a DNA-protein complex. Such DNA-protein complexes include DNA complexed with a ligand that interacts with a target cell surface receptor. Cell surface receptors are thus utilized as naturally existing entry mechanisms for the specific delivery of genes to selected mammalian cells. It is known that most, if not all, mammalian cells possess cell surface binding sites or receptors that recognize, bind and internalize specific biological molecules, i.e., ligands. These molecules, once recognized and bound by the receptors, can be internalized within the target cells within membrane-limited vesicles via receptor-mediated endocytosis. Examples of such ligands include but are not limited to proteins having functional groups that are exposed sufficiently to be recognized by the cell receptors. The particular proteins used will vary with the target cell.

Typically, glycoproteins having exposed terminal carbohydrate groups are used although other ligands such as antibodies or polypeptide hormones, also may be employed. Using this technique the phototoxic protein psoralen has been conjugated to insulin and internalized by the insulin receptor endocytotic pathway (Gasparro, Bio-chem. Biophys. Res. Comm. 141(2), pp. 502–509, Dec. 15, 1986); the hepatocyte specific receptor for galactose terminal asialoglycoproteins has been utilized for the hepatocyte-specific transmembrane delivery of asialoorosomucoid-poly-L-lysine non-covalently complexed to a DNA plasmid (Wu, G. Y., J. Biol. Chem., 262(10), pp. 4429–4432, 1987); the cell receptor for epidermal growth factor has been utilized to deliver polynucleotides covalently linked to EGF to the cell interior (Myers, European Patent Application 86810614.7, published Jun. 6, 1988); the intestinally situated cellular receptor for the organometallic vitamin $B_{12}$-intrinsic factor complex has been used to mediate delivery to the circulatory system of a vertebrate host a drug, hormone, bioactive peptide or immunogen complexed with vitamin $B_{12}$ and delivered to the intestine through oral administration (Russel-Jones et al., European patent Application 86307849.9, published Apr. 29, 1987); the mannose-6-phosphate receptor has been used to deliver low density lipoprotiens to cells (Murray, G. J. and Neville, D. M., Jr., J. Bio. Chem. Vol 225 (24), pp. 1194–11948, 1980); the cholera toxin binding subunit receptor has been used to deliver insulin to cells lacking insulin receptors (Roth and Maddox, J. Cell. Phys. Vol. 115, p. 151, 1983); and the human chorionic gonadotropin receptor has been employed to deliver a ricin a-chain coupled to HCG to cells with the appropriate HCG receptor in order to kill the cells (Oeltmann and Heath, J. Biol. Chem, vol 254, p. 1028 (1979)). Ligands selected from biotin, biotin analogs and biotin receptor-binding ligands, and/or folic acid, folate analogs and folate receptor-binding ligands to initiate receptor mediated transmembrane transprot of the ligand complex, as described in U.S. Pat. No. 5,108,921.

Generally, a ligand is chemically conjugated by covalent, ionic or hydrogen bonding to the nucleic acid. A ligand for a cell surface receptor may be conjugated to a polycation such as polylysine with ethylidene diamino carbodiimide as described in U.S. Pat. No. 5,166,320, and as exemplified in detail below. DNA may be attached to an appropriate ligand in such a way that the combination thereof or complex remains soluble, is recognized by the receptor and is internalized by the cell. The DNA is carried along with the ligand into the cell, and is then expresssed in the cell. The protein conjugate is complexed to DNA of a transfection vector by mixing equal mass quantities of protein conjugate and DNA in 0.25 molar sodium chloride. The DNA/protein complex is taken up by cells and the gene is expressed.

Delivery of the foreign DNA into the target cell may also be achieved via the DNA construct's association with an endosomal disruption agent, such as the influenza hemagglutinin fusogenic peptide. The fusogenic peptide of the HA molecule is a modified form of HA which retains two important functions of HA. It allows for fusion of the targeted DNA/ligand complex to the cell membrane, but without the host cell sialic acid-binding specificity of the natural molecule. Instead, host cell binding specificity is conferred by the ligand/receptor interaction. The modified HA fusogenic peptide also retains the HA function of endosomal uptake, thus allowing for uptake of the complex into the host cell via membrane fusion, and the endosomal escape function of HA, which allows for escape of the enveloped DNA from the endosomal/lysosomal destruction pathway. The fusogenic peptide may include the HA amino acid sequence GLFGAIAGFIGAGTGGMIAGGGC.

Lipsomal Transfer of a Biological Agent

One suitable complex for delivery of a biological agent to a cell according to the invention utilizes liposomes. Liposomes have been used for non-viral delivery of many substances, including nucleic acids, viral particles, and drugs. A number of reviews have described studies of liposome production methodology and properties, their use as carriers for therapeutic agents and their interaction with a variety of cell types. See, for example, "Liposomes as Drug Carriers," Wiley and Sons, NY (1988), and "Liposomes from Biophysics to Therapeutics," Marcel Dekker, NY (1987). Several methods have been used for liposomal delivery of DNA into cells, including poly-L-lysine conjugated lipids (Zhou et al., Biochim. Biophys. Acta. 1065:8–14, 1991), pH sensitive immunoliposomes (Gregoriadis, G., Liposome Technology, Vol I, II, III, CRC, 1993), and cationic liposomes (Felgner et al., Proc. Natl. Acad. Sci., USA, 84:7413–7417, 1987). Positively charged liposomes have been used for transfer of heterologous genes into eukaryotic cells (Felgner et al., 1987, Proc. Nat. Aca. Sci. 84:7413; Rose et al., 1991, BioTechniques 10:520). Cationic liposomes spontaneously complex with plasmid DNA or RNA in solution and facilitate fusion of the complex with cells in culture, resulting in delivery of nucleic acid to the cell. Philip et al. 1994, Mol. and Cell. Biol. 14:2411, report the use of cationic liposomes to facilitate adeno-associated virus (AAV) plasmid transfection of primary T lymphocytes and cultured tumor cells.

Delivery of an agent using liposomes allows for noninvasive treatment of diseases. Targeting of an organ or tissue type may be made more efficient using immunoliposomes, i.e., liposomes which are conjugated to an antibody specific for an organ-specific or tissue-specific antigen. Thus, one approach to targeted DNA delivery is the use of loaded liposomes that have been made target-specific by incorporation of specific antibodies on the liposome surface.

The term "liposome", as used herein, is also intended to encompass liposomes which are composed of several (e.g., 2–3) concentric bilayers which define several individual aqueous compartments. Liposomes useful in the invention are composed of phospholipid molecules. Lipid bilayer structures useful in the invention are preferably circular structures.

a) Preparation of Liposomes

Liposomes and immunoliposomes may be prepared according to a variety of techniques, e.g., detergent dialysis or the formation of a water-in-oil emulsion, slow swelling in nonelectrolytes, dehydration followed by rehydration, dilution or dialysis of lipids in the presence of chaotropic ions, and mechanical preparation techniques such as freeze-thaw cycling.

Removal of detergent molecules from aqueous dispersions of phospholipid/detergent mixed micelles represents one way of producing liposomes (see J. Biol Chem. 246:5477 (1971) herein incorporated by reference). As the detergent is removed, the micelles become progressively richer in phospholipid and finally coalesce to form closed, single bilayer vesicles. Detergents commonly used for this purpose include bile salts and octylglycoside. Because this method does not involve the use of organic solvents and sonication, it is particularly useful for entrapping macromolecules, such as nucleic acids, which are sensitive to the presence of organic solvents or are structurally altered by sonication.

Another method of preparing liposomes is the reverse phase evaporation method detailed in U.S. Pat. No. 4,235,871, which is incorporated herein by reference.

Liposomes may also be prepared via hydration in the presence of a solvent. Multi-lamellar vesicles (MLVs) with high encapsulation efficiency can be prepared by hydrating the lipids in the presence of an organic solvent. The two phases are emulsified by vigorous mixing (vortexing) and then the organic phase removed by passing a stream of nitrogen gas over the emulsion. As the solvent evaporates, liposomes form in the aqueous phase.

Mechanical preparation methods, e.g., shaking by hand, sonication, French pressure freeze-drying, membrane extrusion, freeze-thawing, changing pH, calcium inducing, and micro emulsion techniques, have been used for the preparation of liposomes.

b) Preparation of Immunoliposomes

Liposome targeting based on antibody/antigen recognition has been utilized in the prior art in the development of targeted delivery systems for delivery of various bioactive agents to a target site. Antibody-directed liposomes, or immunoliposomes, are used for this purpose. Antibody molecules are predominantly hydrophilic compounds with no affinity for the hydrophobic liposome membrane. Immunoliposomes can be used to deliver hundreds or more units of intraliposomal contents into an individual target cell. Immunoliposomes administered according to the invention are administered intravenously, intraperitoneally or directly to the target tissue or organ, at a dosage that is appropriate for the amount of biological agent or genetic material that is encapsulated by the liposome. Immunoliposome dosage will therefore vary from about 5 mg/kg body weight to about 1 gm/kg body weight, and may be in the range of 100 mg–500 mg/kg body weight.

As used herein, an immunoliposome comprises a liposome conjugated to an immunoglobulin molecule. Where enhancement of specificity of the immunoliposome for the target site is desired, the immunoliposome may include antibodies of several different specificities, each cognate antigen being found at the target site. Such multiple specificity may also be conferred using bifunctional or trifunctional antibodies (see, e.g., U.S. Pat. No. 5,237,743, hereby incorporated by reference).

Methods are known in the prior art for preparing immunoliposomes. Immunoliposomes are prepared, for example, by adsorption of proteins (e.g., immunoglobulin) on the liposomal surface; incorporation of native protein into the liposome membrane during its formation (e.g., by ultrasonication, detergent dialysis or reverse phase evaporation); covalent binding (direct or via a spacer group) of a protein to reactive compounds incorporated into the liposomes membrane; noncovalent hydrophobic binding of modified proteins during liposome formation or by the incubation with preformed liposomes); and indirect binding, including covalent binding of immunoglobulin protein via a polymer to the liposome (see Torchilin, V. P. CRC Critical reviews in Therapeutic Drug Carrier Systems, vol. 2(1), hereby incorporated by reference).

Immunoliposomes may be prepared according to the following procedure.

1. Covalent Coupling of Antibody with NGPE.

0.6 mg N-Glutaryl phosphatidylethanolamine (NGPE) is dissolved in 0.5 cc 2-[N-morpholino]ethanesulfonic acid hemisodium salt (MES) buffer (in 0.016M octylglucoside in 50 mM MES). After the addition of 4.8 mg 1-ethyl-3-(3-dimethylaminopropyl)-carbodiimide (EDC) and 6 mg N-hydroxysulfosuccinimide (HSSI), the resulting mixture is incubated at room temperature for 5 min. The antibody solution is then added (0.36 mg/ml). The pH of the mixture is then adjusted to 8.0 with 1M NaOH. The reaction mixture is incubated at 4° C. for 8–12 hour with mixing. The resulting NGPE-antibody conjugate is then dialyzed overnight against PBS, pH 7.4 to remove octylglucoside and other excess reagents.

2. Preparation of Immunoliposomes by detergent dialysis.

Liposomes are prepared from a mixture of egg phosphatidylcholine (PC) and cholesterol (Ch) in chloroform in the molar ratio 1:1. The lipid mixture (30 mg PC/17.96 mg Ch) is dried with argon, then vacuum dried for 2 hour and resuspended in 4 cc phosphate buffered saline (PBS) containing 0.016M octylglucoside with brief ultrasonication. The solution of NGPE-modified antibody (0.7 mg/ml) is added to solubilized lipids. The mixture is dialyzed overnight against PBS (pH 7.4) to remove detergent. The resulting liposomes are extruded through a Nucleopore filter (0.6, 0.4, and 0.2 μm). The same method is used for preparation of liposomes without NGPE-antibody solution.

c) Loading of Immunoliposomes

Loading of compounds into liposomes may be achieved by one or more of a variety of active and passive methods. Passive loading by entrapment is employed where relatively low concentrations of the DNA construct is desired. Loading of high concentrations of DNA in liposomes may require active loading methods, e.g., as described in U.S. Pat. No. 5,129,549, herein incorporated by reference, in which a chemical gradient is created across the liposome membrane that results in trapping of the DNA in the internal aqueous phase of the liposome.

Liposome/DNA formulations are characterized by measurements of particle size, lipid concentration, and pH by standard methods as described above. DNA incorporation into the composition may be determined by inclusion of radiolabeled tracer in the composition. The amount of liposome-entrapped DNA is then determined by gel permeation chromatography using BioRad A-15M resin. The liposomal DNA fraction is calculated from the amount of radiolabel present in the void volume of the column, and the percentage of liposomal DNA from the ratio of label eluting in the void volume to the remaining label eluting from the column.

Preparation of Antibodies

Immunoglobulin molecules useful in the invention include whole antibody, or any antibody fragment, for example, a F(ab')2, Fab, and/or an Fv fragment of an antibody molecule. In addition, any variable region specificity of an antibody molecule is useful according to the invention.

A F(ab')2 fragment is that portion of an antibody molecule which contains the complete antigen-combining site, consisting of two light chains and part of each heavy chain, and is produced by enzymatic digestion, e.g., using pepsin, such that the heavy chain disulfide bonds remain intact in the F(ab')2 fragment. A Fab fragment consists of a single light chain and a part of a heavy chain disulfide bonded together. Fab is produced by enzymatic digestion, e.g., using papain, such that about one-half the F(ab')2 antigen binding fragment is generated. An Fc fragment is that portion of an antibody that is responsible for binding to antibody receptors on cells and the C1q component of complement. The Fc fragment is the portion of the antibody molecule that remains after papain digestion. An Fv fragment is that portion of an antibody consisting of the variable region of a Fab fragment.

Antibodies useful in the invention may be obtained through conventional polyclonal or monoclonal antibody preparation techniques. Antigen may be obtained from cells of the species toward which the antibodies are to be directed. Such species are preferably vertebrate, more preferably mammalian, and most preferably human. For antibodies directed toward human intracellular antigens, immortal cell lines represent a convenient source of such antigen.

To generate monoclonal antibodies, murine spleen cells from immunized animals are fused with an appropriate myeloma cell line. Fused cells are cultured in selective growth medium to establish hybridoma colonies, each colony secreting an antibody of interest. Culture supernatants from each colony are then tested for antibody specificity. Positive cultures are identified and expanded. See Kohler et al., Nature 256:495 (1975), hereby incorporated by reference.

EXAMPLE 3

Viral Vectors Useful According to the Invention

The invention contemplates delivery of recombinant DNA to a target cell. Accordingly, such delivery may be achieved using any suitable recombinant vector. Recombinant retroviral vectors as well as other DNA transfer vectors can be used in practice of the present invention.

A recombinant viral vector of the invention will include DNA of at least a portion of a retroviral genome which portion is capable of infecting the target cells and a functional gene operatively linked thereto. As used herein, "functional" or "expressible" gene means a gene encoding a protein having a biological effect. By "infection" is generally meant the process by which a virus transfers genetic material to its host or target cell. Preferably, the retroviral vectors used in the construction of a vector of the invention is not an infectious viral particle and is also rendered replication-defective to remove the effects of viral replication on the target cells.

Suitable retroviral vectors for practice of the invention include but are not limited to, for example, adenoviral vectors, adeno-associated viral vectors and SV40 viral vectors; suitable retroviral vectors include but are not limited to pLJ, pzip, pWe and pEM, well known to those skilled in the art.

The genetic material to be recombined with the retroviral vector or transferred through other methods of the invention is preferably provided through conventional cloning methods, i.e., cDNA, through overlapping sequences or any other suitable method yielding the desired clone.

EXAMPLE 4

Preparation of Antibody-Polylysine-DNA Complexes and Introduction of DNA into Hematopoietic Cells According to the Invention 1. Preparation of monoclonal antibodies-polylysine conjugates Monoclonal antibodies to various human hematopoietic cell surface markers were conjugated to poly (L-lysine) (MoAb-PL) with a 196–278 chain length. Ligand: polylysine: DNA complexes were constructed following the procedures first described by Wu and Wu (1987) as subsequently modified by Birnstiel and coworkers (Wagener et al., 1990; 1991). The ratio of ligand: polylysine and peptide: polylysine per DNA targeting complex can be determined by titration on a cell type to cell type basis.

Antibody-polylysine conjugates were synthesised through disulphide linkages, which were formed using the bifunctional reagent 3-(2-Pyridylilthio) propionic acid N-hydroxysuccinimide ester (SPDP: Sigma Chemical Co.) using a modification of the protocol described by Wagenr E. et al., Proc. Natl. Acad. Sci. U.S.A., 87, 3410–3414, 1990. Antibodies were purified prior to conjugation and transferred into phosphate or N-(2-hydroxyethyl) piperazide N'-(2-hydroxyethyl) piperazine N'-2-(ethanesulfonic acid), HEPES buffered saline solutions. Poly-L-lysine hydrobromide salts with an average chain length of 200 monomer units and a range of 117–234 units were obtained from Sigma Chemical Co.

2. SPDP modification of antibody

SPDP, solubilized in dried acetonitrile at a concentration of 20 mM was added to antibodies at a molar ratio of 10:1, the antibodies being in either HBS (pH 7.9) or PBS (pH 7.5) solutions at concentrations of 1–5 mg/ml. The reactants were mixed at room temperature for 1 hr, after which the excess and free linker acid released during the antibody labelling were removed by size exclusion chromatography (G25: Pharmacia), the collected labelled antibody was then stored at +4° C. The pyridine-2-thione content of labelled antibody was determined by measuring the increase in 343 nm absorbence in the presence of Dithiothreitol (DTT), antibody concentration was determined by A280 measurement, (correcting for the effect of pyridine-2-thione content, Carlsson, J. et al., Biochem. J., 173,723, 1978) using an extinction coefficient of 1.7 Au 280 ml/mg antibody. The level of linker loading was then determined by relating the pyridine-2-thione content to the antibody content. Typically, ratios of 2–6 linker units per antibody were obtained.

3. Modification of poly-L-Lysine

Polylysine solubilized in 50 mM Hepes pH 7.9 at a concentration of 20 mg/ml, was reacted with SPDP (prepared as previously described), the SPDP being added at a 5:1 molar excess. The reactants were mixed at RT for 1 hr, after which the solution pH was adjusted to 5 by the addition of 1M Sodium acetate pH5.0.

Excess SPDP and free linker acid were removed by size exclusion chromatography (G25: Pharmacia equilibrated in 20 mM sodium acetate buffer pH 5.0) and the pyridine-2-thione content of the polylysine determined as previously described. This value was related to the original quantity of polylysine added to the reaction mixture to give a value for the linker loading on the polylysine. Typically values between 1–4 were obtained. The pH of the collected polylysine pool was adjusted to 7.9 by the addition of 1M Hepes buffer pH 7.9, and stored at +4° C.

The labelled polylysine solution was reduced by the addition of a 10–15 molar excess of DTT and reacted for 30–60 min's at RT in order to produce free thiol groupings. The pH of the solution was then adjusted to 5.0 by the addition of 1M sodium acetate pH 5.0 and excess DTT removed by size exclusion chromatography (G25: Pharmacia). The free thiol levels of the polylysine pools were determined using 5,5'-Dithio-bis (2Nitrobenzoic acid) Ellman's reagent (Deakin H. et al., Biochem. J., 89, 296, 1963).

4. Conjugation of antibody with polylyshine

Labelled antibody was diluted to a level of <=1 mg/ml with 50 mM Hepes pH 7.9 and glycerol added to 20% v/v. Labelled Polylysine was added at a 5:1 excess to labelled antibody and the reactants mixed for 16–20 hrs. at 10° C. (the antibody/polylysine ratios being based on measured antibody concentrations, and assumed polylysine concentration). The conjugation levels achieved were determined by measuring the 343 nm absorbence and comparing to that in the original solution. The increases in 343 nm absorbence was then related to the original pyridine-2-thione content, and the amount of free thiol added to the original conjugation mixture. Typically the results showed that 50–100% of the available dipyridyl groups were reacted and that 10–50% of the free thiol added were reacted in the various conjugation mixtures, suggesting polylysine to antibody levels of between 2 and 5.

5. Purification of conjugates

Conjugates were purified by cation exchange chromatography (Fractogel EMD $SO_3$ E. Merck). Prior to purification NaCl was added to the conjugate mixtures to a level of 0.6M by the addition of 3M NaCl 50 mM Hepes pH 7.9. The chromatography columns were equilibrated in 0.6M NaCl 50 mM Hepes pH 7.9 prior to sample loading and a 0.6–3.0M NaCl gradient was run over the column in order to elute the conjugated material, conjugate being eluted been 1.0 and 2.5M NaCl.

The presence of conjugate in the eluted material was determined by SDS PAGE, in which samples were loaded in reduced and non-reduced states. Conjugates were defined as samples which did not enter the gel under non reducing conditions but showed normal antibody profiles under reducing conditions.

The binding specificity of all antibody-polylysine conjugates was then compared with antibody alone by FACS analysis to ensure that chemical modification had not diminished or altered the binding specificity of the antibody polylysine conjugates.

6. Preparation of antibody-polylysine: DNA complexes

RSVLuc, a DNA plasmid containing the luciferase gene under control of the RSV promoter (provided by Dr. M. Cross), as a reporter gene were used. The appropriate amount of DNA was diluted in HBS (120 mM NaCl, 20 mM Hepes, pH 7.4) and the MoAb-Pl solution added in HBS dropwise with constant mixing. The complex mixture was allowed to stand at least for 30 min at room temperature. The amount of DNA that bound to different MoAb-PL preparations differed according to the binding characteristics of each preparation (the mass ratio of MoAb-PL to DNA ranges from 0.5:1 to 2:1). However, the DNA concentration in the complex should not exceed 20 µg/ml otherwise precipitation of the complex will occur. In a typical experiment the complex was formed by mixing 300 µl HBS solution contains 5 µg of RSVLuc with 100 µl of HBS solution containing 10 µg of HB2-PL278 (anti-CD7).

7. Incubation conditions of hematopoietic cells with the monoclonal antibody-polylysine/DNA complex and the Influenza virus haemangglutinin HA-2 N-terminal fusogenic peptide $5 \times 10^6$ cells resuspended in 3 ml of RPMI/5% FCS supplemented with 2 mM glutamine, 100 U/ml penicillin and 100 µg/ml streptomycin. The MoAb-PL/DNA complex solution was added at 5–10 µg MoAb/$10^6$ cells (2 ml of the HB2-PL/DNA complex solution in the case of the typical experiment cited above). An influenza fusogenic peptide (GLFGAIAGFIGAGTGGMIAGGGC SEQ ID NO.1; synthesized by Neosystem, Strasbourg, France) was added at a final concentration of 30 µM. The tube containing the cell suspension was gassed with 5% $CO_2$, the cap of the tube tightened, and the tube left to stand on wet ice for 2 h with gentle shaking every 30 min to allow for saturation of all the relevant cell surface marker with the antibody complex to occur. The tubes were transferred to a 5% $CO_2$ incubator and left for 45 min to allow for internalization and cycling of the MoAb-PL/DNA.

8. Electric Shock Procedure

At the end of incubation the cells were washed once with RPMI/5% FCS and once with ice cold PBS by spinning at 800 g for 10 min to remove non-bound MoAb-Pl/DNA complex. The cells were resuspended in 0.5 ml of electroporation-type Hepes buffer (120 mM KCl, 0.15 mM $CaCl_2$, 10 mM $KHPO_4/KH_2PO_4$, 5 mM $MgCl_2$, 25 mM Hepes, pH 7.4) (pipetting the cells should be avoided at this stage; they were easily resuspended by carefully swirling the tubes). The cell suspension was transferred into a 4 mm interelectrode distance sterile electroporation cuvette. The cuvettes containing the cell suspensions were kept on ice for approximately 2 min. Before electric shock treatment the outside surface of the cuvettes was dried thoroughly to avoid a short circuit. A single voltage pulse was applied at the conditions of 300 V and 250 µF capacitance using a Gene-Pulser system (Bio-rad). After the electric shock treatment the cells were cooled on ice for 2 min then carefully removed using a sterile plastic Pasteur pipette into a fresh tube. The cells were diluted 10× (5 ml total) with RPMI/5% FCS. Cells were collected by low speed centrifugation (150 for 4 min). The cells were resuspended in 3 ml RPMI/40% FCS, placed in a 12 well culture plate and incubated for 24 h before assessing the luciferase activity. Cell viability was determined by dye exclusion Vectors targeted to stem cells would contain different regulatory sequences such as Locus Control Regions (LCRs) (see European Patent Application 332667) depending on whether the therapeutic benefit was to be obtained as a result of cell specific expression of the delivered gene, or whether expression was desirable in all cells through the induction of a strong ubiquitously active promoter. For example, the efficient delivery of therapeutically effective nucleic acids to hematopoietic stem cells would be of immense clinical value, for example in the correction of genetic diseases such as lysosomal storage disorders, hemophilia and haemoglobinopathies; for the modification of cells of the immune system to provide protection against pathogenic organisms such as HIV, to incite an immune response, to modulate an inflammatory or autoimmune response, or to boost the production of agents of therapeutic benefit such as calcitonin, α1-antitrypsin or a variety of growth factors or cytokines.

Clinically, there is a great advantage in targeting genes to cells of the hematopoietic lineage, since the cells can be obtained in large numbers from blood, using established procedures, transfected ex vivo, then replaced after transfection into the patient. This applies particularly to T-cells which represent as much as 90% of the lymphocyte subpopulation of circulating white blood cells, but also to stem cells which can be mobilised in significant numbers in peripheral blood as a result of prior treatment of the patient with GCSF (see Demuynck et al., 1992). Stem cells are also present in cord blood and bone marrow.

Using established technology stem cells may only be used in DNA transfection after extensive enrichment procedures (See, for example, European Patent Applications 0 455 482 and 0 451 611, which disclose a method for separating stem cells from a population of hematopoietic cells). However, even current safe non-viral transfection protocols permit only a small percentage of such stem cells to be transfected.

EXAMPLE 5

Introduction of DNA into isolated Human Primary T-Cells According to the Invention 1. Preparation of mononuclear cells from peripheral and cord blood Lymphocytes An equal volume of phosphate-buffered saline (PBS) was added to a heparinized blood sample and mixed well. Carefully and gently, 10 ml of the cell suspension was layered onto 10 ml of J-PREP solution (1.077 g/ml density, TechGen International) by resting the tip of the pipette against the wall of a universal tube, taking care not to disturb the surface meniscus. The preparation was centrifuged at 400 g for 20 min at room temperature. This produced a pellet of red cells and granulocytes at the bottom of the tube, a clear layer of the separation medium, a cloudy interface layer containing the mononuclear cells (MNC) and a plasma/PBS layer on top. The interface layer was harvested using a Pasteur pipette and centrifuged at 800 g for 10 min at room temperature to collect the MNC pellet. The cells were washed twice with RPMI/5% heat inactivated fatal calf serum (RPMI/5% FCS) by centrifugating at 800 g for 5 min at room temperature.

2. Isolation of CD34+ cells from mononuclear cells of cord blood a) Labeling of cells with biotinylated anti-CD34 monoclonal antibody The CERATE LC system (CellPro Incorporated, Wash., USA) uses an avidin-biotin immunoaffinity process to positively select CD34+ cells from a heterogenous cell population. Before starting the separation procedure primary anti-CD34 monoclonal antibody (MoAb) was removed from the freezer and allowed to thaw slowly undisturbed to room temperature (30 min). The MNC were washed twice with PBS/1% bovine serum albumin (PBS/1% BSA) and resuspended in 1 ml of the same buffer. The cells were mixed with the anti-CD34 MoAb to give a final concentration of 20 µg/ml and incubated at room temperature for 20 min. After the incubation the cells were diluted to 10 ml with PBS/1% BSA and washed twice with the same buffer by spinning at 500 g for 5 min. Cells were resuspended at a concentration of $10^8$/ml in PBS/5% BSA.

b) Preparation of the avidin column 4 ml of PBS was added to the sample chamber and the system was ensured to be air bubble-free. PBS was allowed to flow into the wash chamber. Another 5 ml of PBS was added to the sample chamber and the wash chamber topped up to 10 ml with PBS. Slowly, the pre-gel was added dropwise to sample chamber (a uniform 0.7 ml bed of pre-gel formed on the bottom of sample chamber above the avidin column which serves to trap tissue debris and cell clumps). 5 ml of PBS was allowed to pass through. 5 ml of PBS/5% BSA solution was added and the flow stopped when the buffer level reached the top of the pre-gel.

3. Cell separation protocol

Antibody-labelled cells were layered onto pre-gel in sample chamber (4 ml maximum) and eluted unabsorbed cells collected in a fresh tube. When cell sample reached the top of the pre-gel, an additional 2 ml of PBS/5% BSA was added to flush any remaining cells into the avidin column. When the remaining buffer reached the top of pre-gel PBS was allowed to flow between the wash chamber and the avidin column (making sure not to allow air into avidin column at this stage). When the PBS in the wash chamber reached 5 ml mark the flow was stopped. A fresh tube containing 1 ml PBS/5% BSA was placed to collect absorbed cells. Flow was started and the avidin column squeezed vigorously 3–5 times. 1 ml PBS was allowed to flow into the collecting tube. The squeeze was repeated and left to flow until all of the PBS was drained from wash chamber. The collected cells were washed twice with RPMI/ 5% FCS and resuspended in 2 ml of the same buffer before counting the cells. The cells were placed in a 95% aire 5% $CO_2$ incubator for 30 min before performing a FACS analysis of CD34+ cells in the collected fraction using a different anti-CD34 MoAb.

Figure 2:
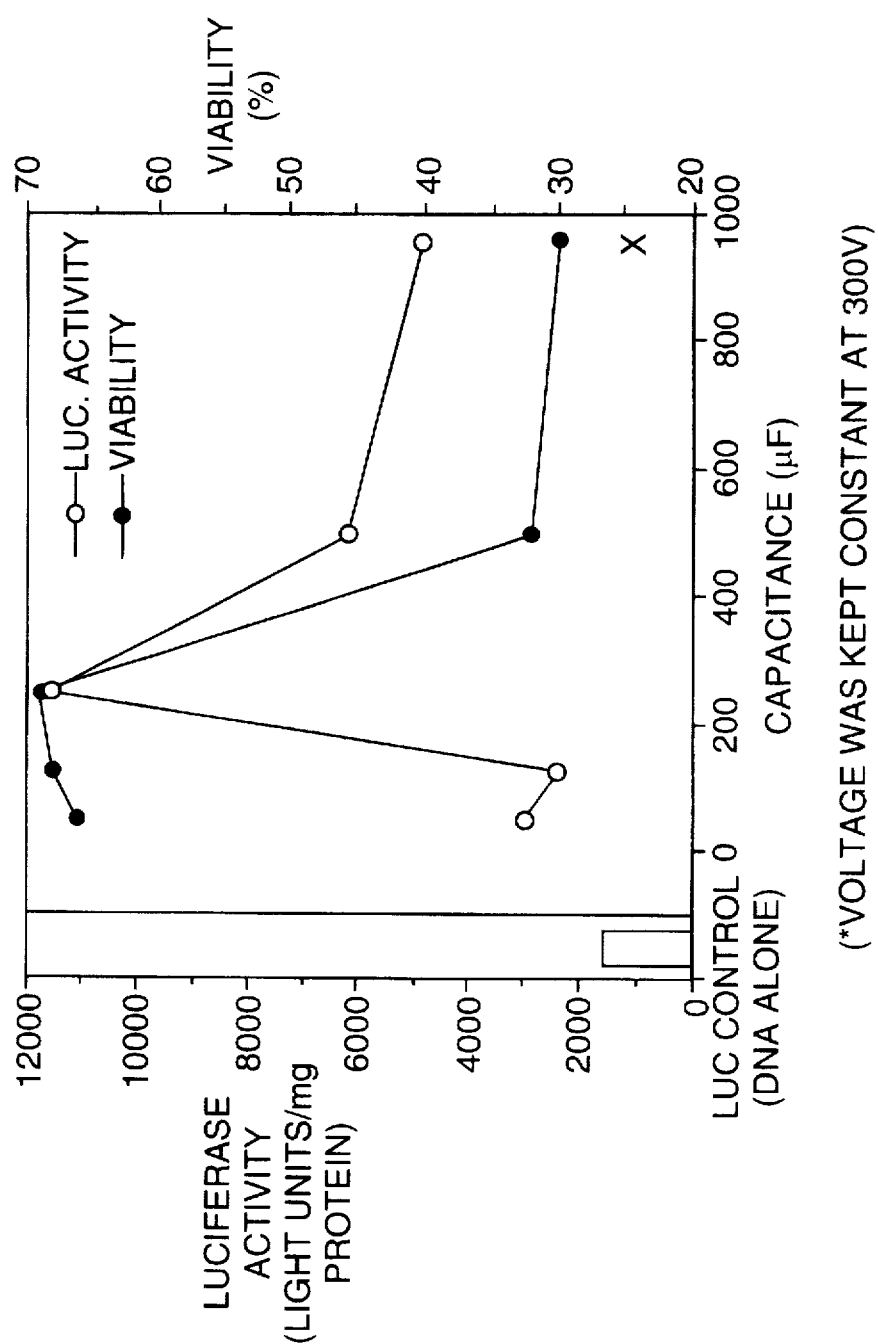
FIG. 2 shows the results of transfection of human T-cells in a total white blood cell population using an anti-CD7 antibody: DNA complex over a range of capacitance values at constant voltage (300v); the letter X indicates the expected viability of electroporated cells.

Human primary T-cells were obtained from human blood, as described above, and subjected to transfection as described with an anti-CD7 antibody:RSVLuc complex according to the method of the invention, in the absence of fusogenic peptide, at a variety of capacitance values on the Bio-Rad gene pulse apparatus. At optimum levels, it can be seen in FIG. 2 that the viability of cells remains essentially unchanged when compared to the control of 0 µF (i.e. no electric field).

EXAMPLE 6

Introduction of DNA into CEM Cells According to the Invention

Figure 3:
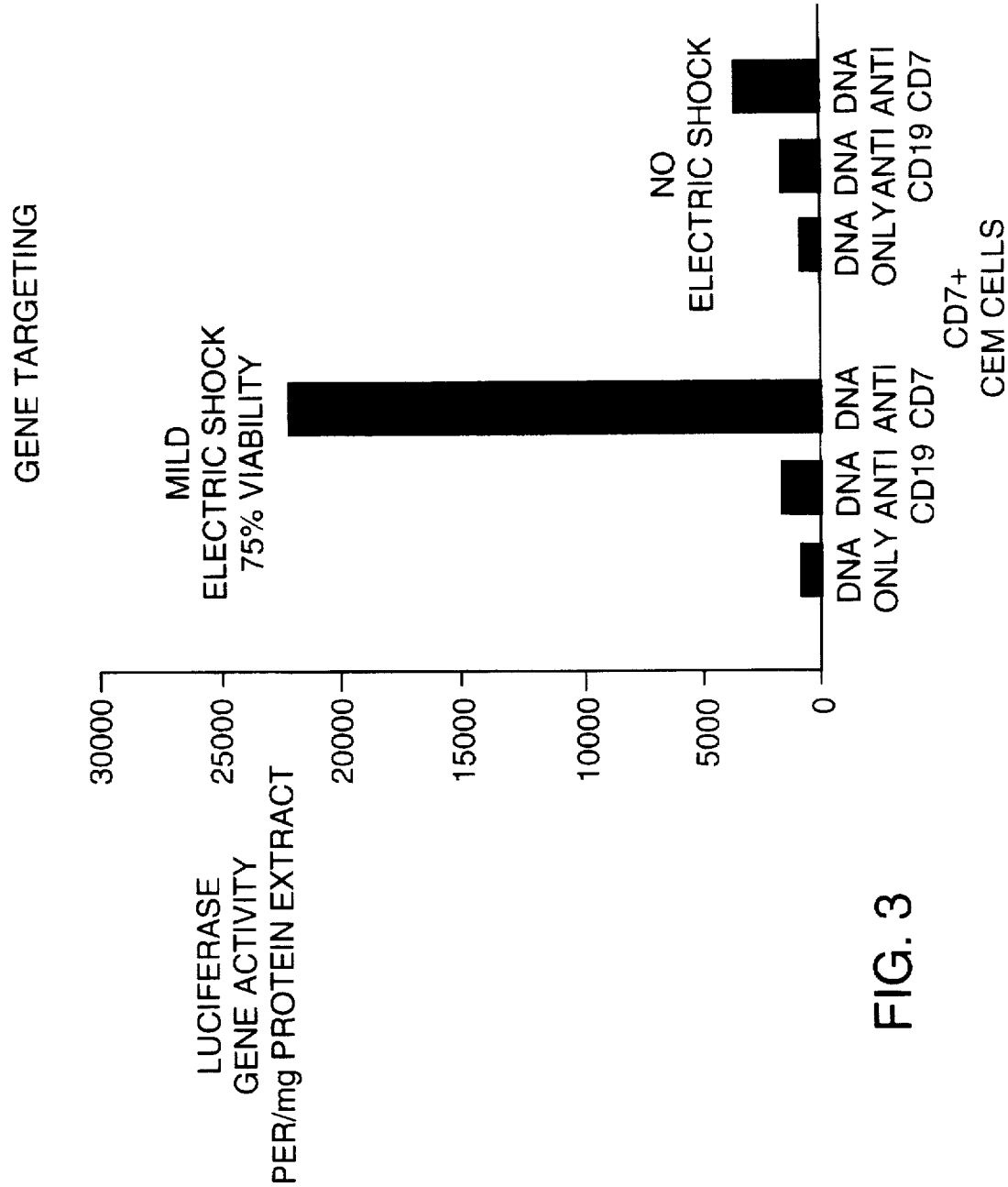
FIG. 3 shows the results of transfection of cell lines with an antibody: DNA complex in the presence or absence of electric shock treatment and demonstrates the specificity of targeting.

CEM cells carrying the CD7 surface marker were transfected with RSVLuc complexed to anti-CD7 and anti-CD19 antibodies, according to the protocol described above. The results are shown in FIG. 3.

As a control, uncomplexed DNA was used to transfect CEM cells in the presence or absence of the electric shock treatment. Luciferase gene activity in the control experiment was very low and, significantly, was not affected by the electric shock treatment. This shows that the electric field used in the present method does not give rise to effective electroporation of the cell membrane.

Likewise, no effect was seen when the electric shock treatment was applied to cells transfected with DNA complexed to anti-CD19. CEM cells are CD 19.

However, a large increase in luciferase gene activity is seen with cells transformed with anti-CD7 complexed DNA upon administration of the electric shock.

EXAMPLE 7

Introduction of DNA into Targeted T-Cells According to the Invention

White blood cells were isolated from whole human blood by centrifugation. The T-cells present in the crude white blood cell preparation were targeted with an anti-CD7:RSVLuc complex, optionally further comprising an influenza virus haemagglutinin fusogenic peptide.

Figure 4A:
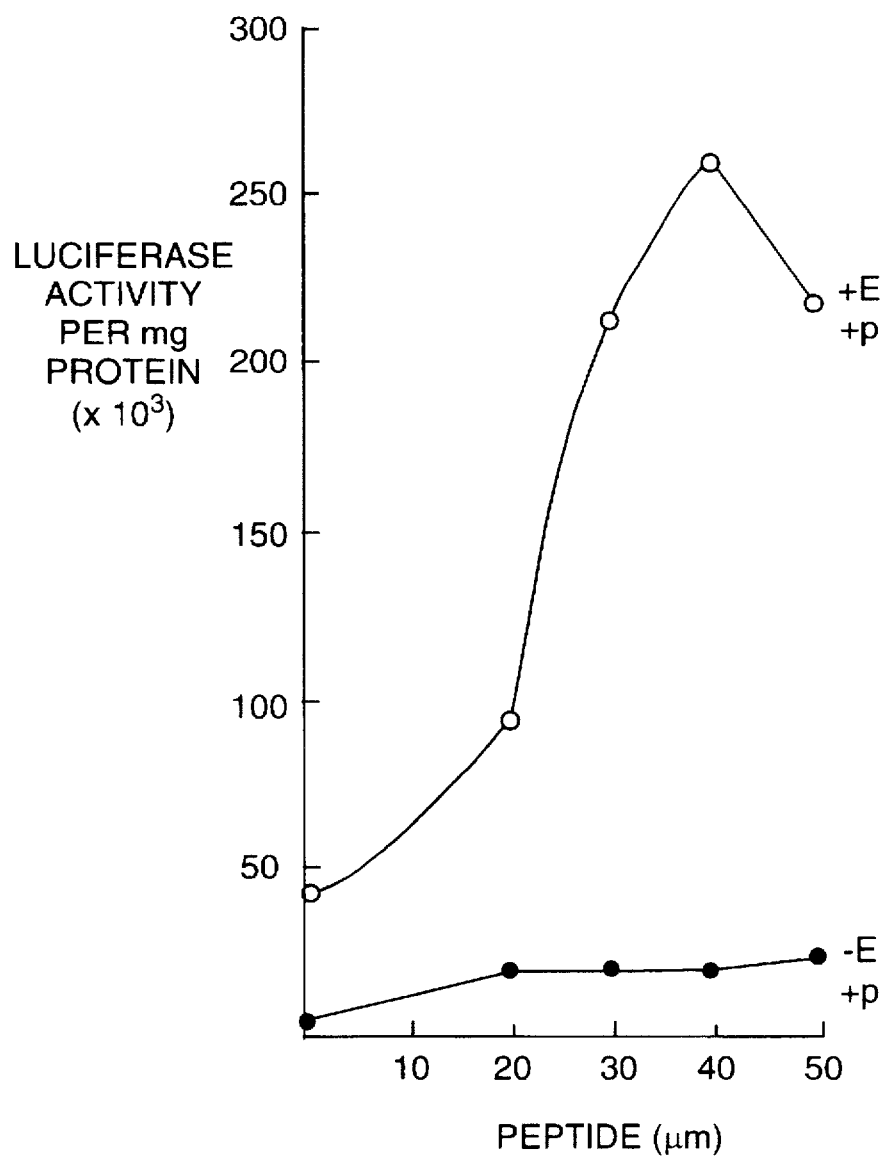
FIGS. 4A and 4B show the results of the transfection of primary human T-cells in a total blood cell preparation using an anti-CD7 antibody: DNA complex (FIG. 4A) and the synergistic effect of a fusogenic peptide (FIG. 4B)
Figure 4B:
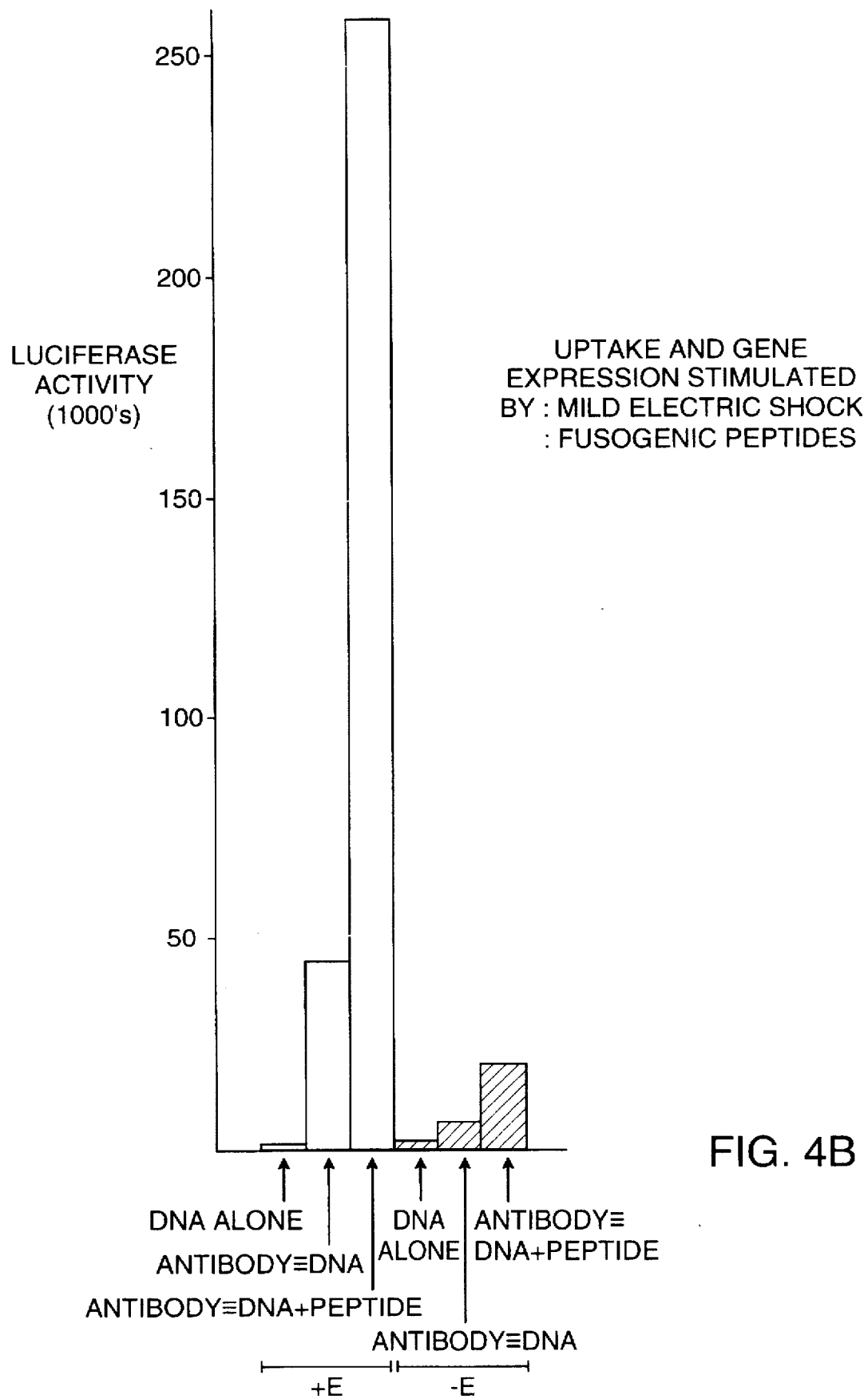

The results, shown in FIG. 4, demonstrate that, in the presence of the electric shock treatment of the invention, vastly superior transfection efficiency is observed. The use of a fusogenic peptide further enhances the efficiency obtainable by the method of the invention.

EXAMPLE 8

Figure 5:
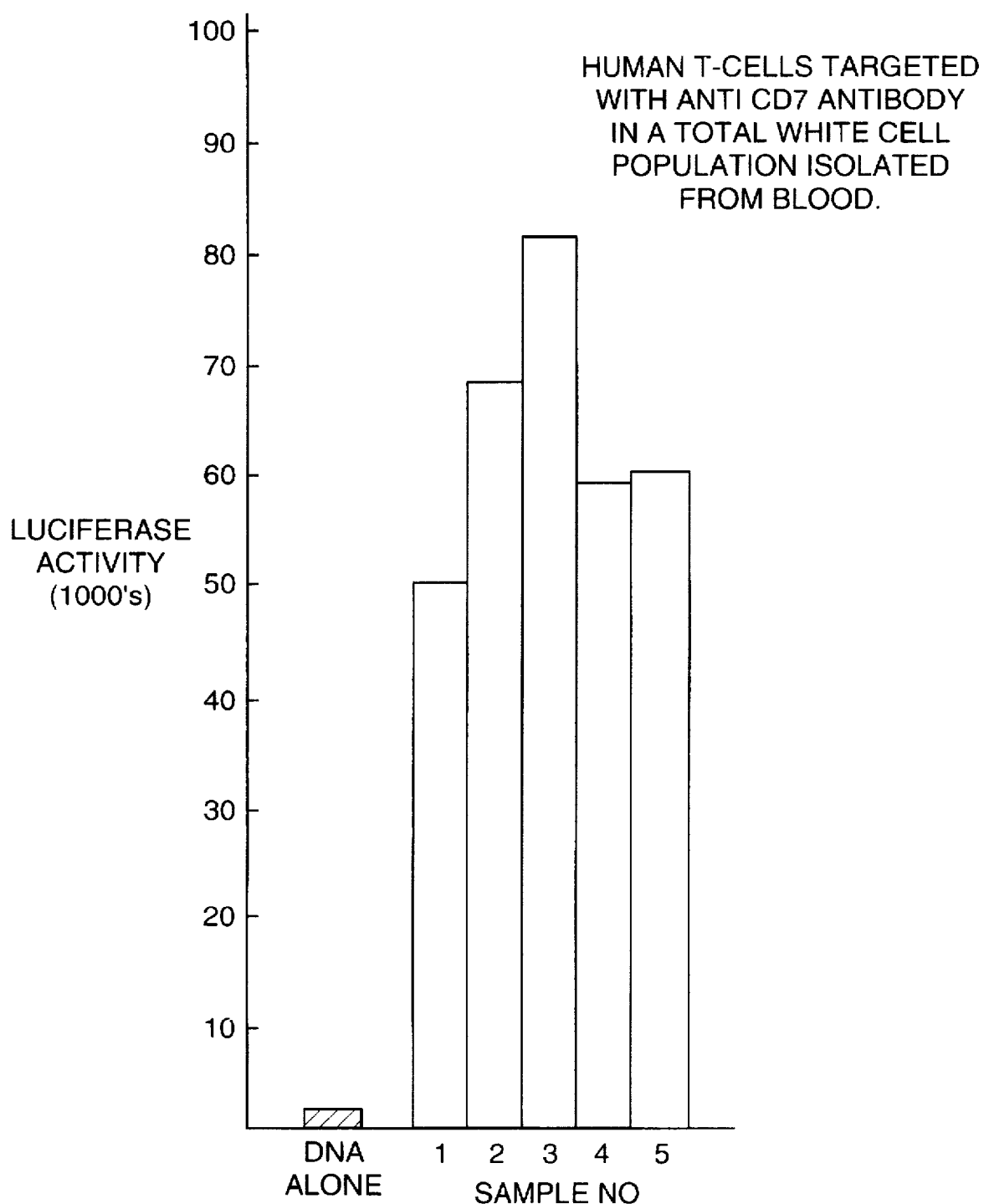
FIG. 5 shows the reproducibility of the results shown in FIG. 4.

The experiment described in Example 7 was repeated five times in order to demonstrate the reproducibility of the results. The data from the five experiments appear in FIG. 5.

EXAMPLE 9

Figure 6A:
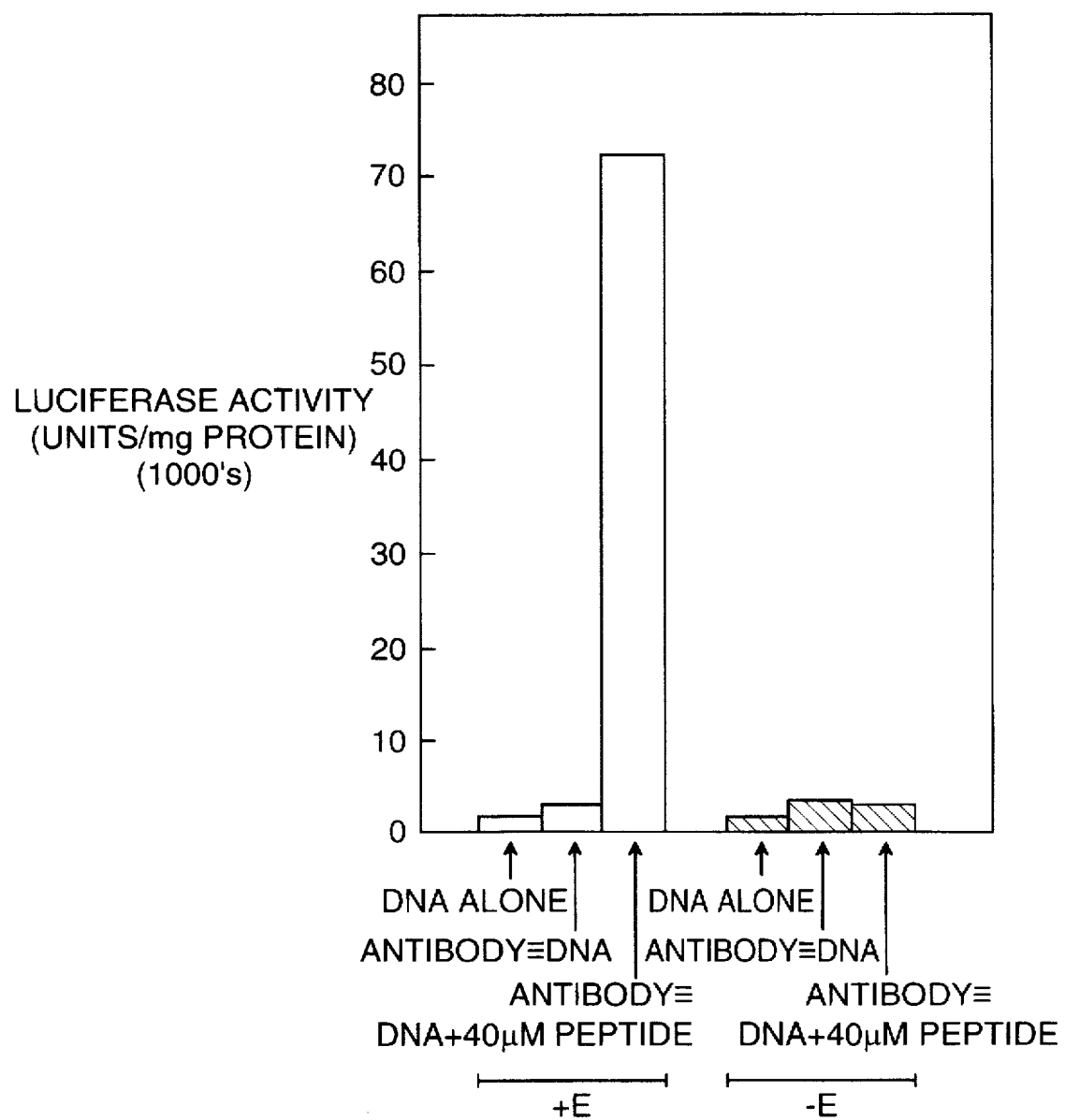
FIG. 6 shows the transfection of human peripheral blood mononuclear cells using an anti-CD33 antibody:DNA complex (FIG. 6A) and an anti-MHC class II antibody:DNA complex (FIG. 6B) and demonstrates synergy between electrical stimulation and the use of a fusogenic peptide.
Figure 6B:
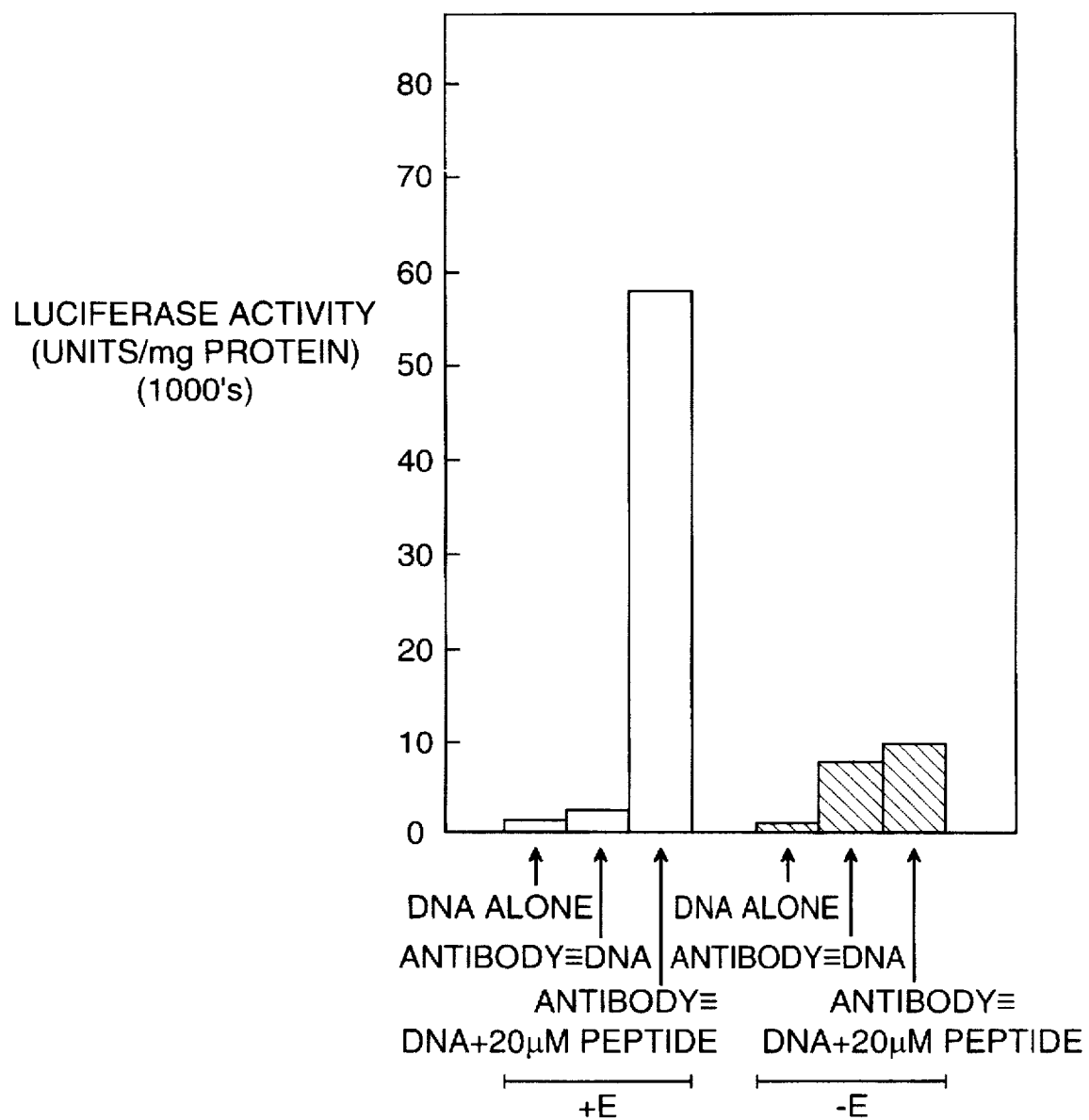

The experiments described in Example 7 were repeated except that white blood cells (PBMNCs) isolated from whole human blood were targeted with an anti-CD33:RSVLuc complex (FIG. 6A) or an anti-MHC class II:RSVLuc complex (FIG. 6B). The results demonstrate the synergistic effect between fusogenic peptide and electric shock treatment in the enhancement of transfection efficiency while maintaining cell viability.

EXAMPLE 10

Introduction of DNA into Targeted Stem Cells According to the Invention

Stem cells in a total white blood cell population (MNCs) isolated from whole human cord blood were targeted with QBEND-10, an anti-CD34 antibody, complexed with RSV-Luc.

Figure 7:
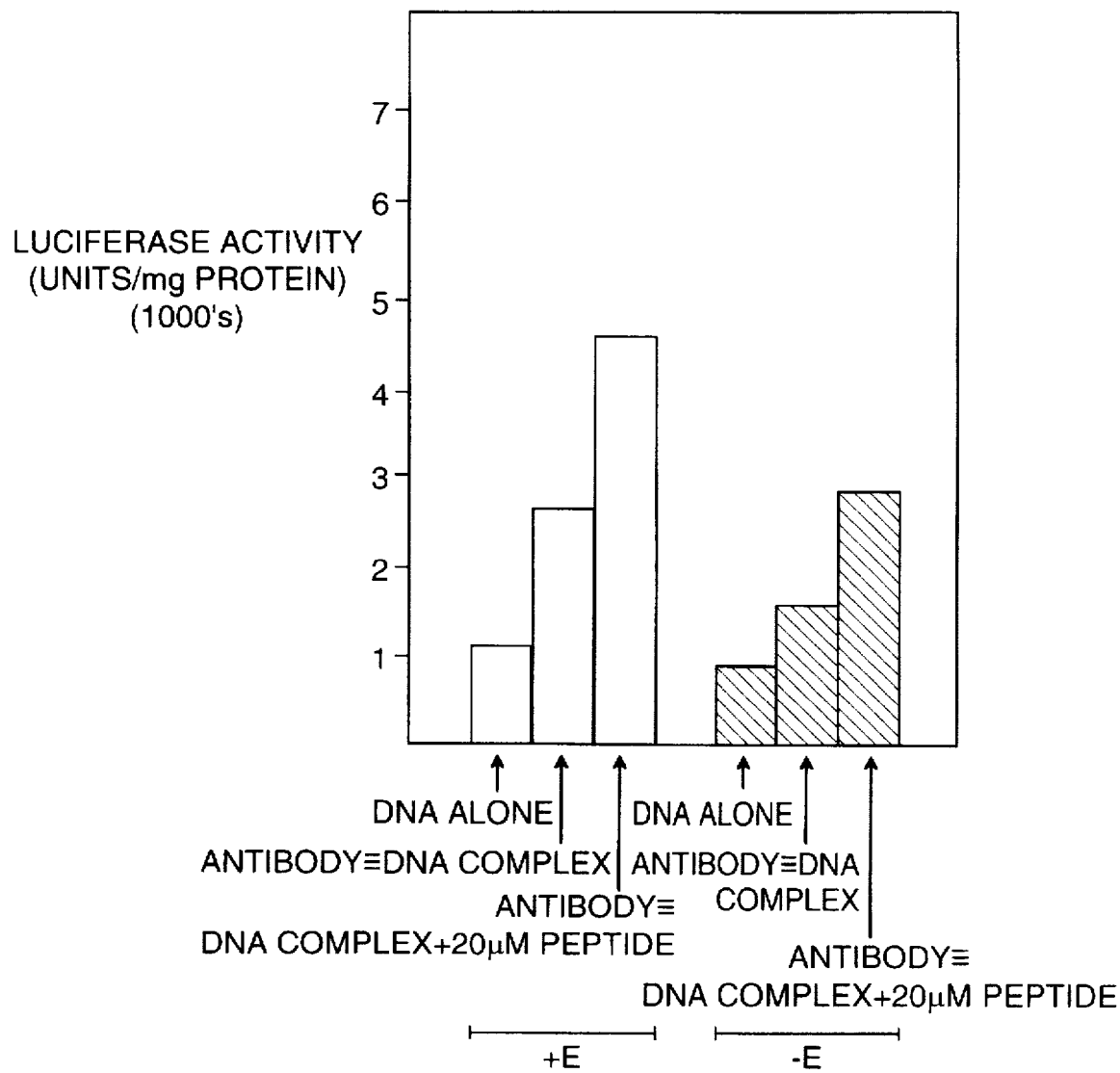
FIG. 7 shows the results of the transfection of primary human stem cells (CD34$^+$) present in total white blood cell preparations (MNCs) from cord blood.

Cells were not fractionated and contained 3.4% CD34 + cells. The effect of the use of electric shock treatment and a fusogenic peptide was assayed. The results are shown in FIG. 7 and demonstrated the enhancement of transfection by the use of an electric field and fusogenic peptide over fusogenic peptide alone.

EXAMPLE 11

Introduction of DNA into Targeted Stem Cells According to the Invention

To demonstrate the specificity of anti-CD34:DNA complex delivery to stem cells in total white blood cell preparations, white blood cells were isolated from human blood and $2.5 \times 10^7$ mononuclear cells incubated with the complexes shown in table 1 for 2 hours at 4° C. The cells were then washed twice for 45 minutes at 37° C. and subjected to electrical shock treatment (except sample D).

Viability was determined and is shown in table 1. It should be noted that the results should be compared to the level for sample D, which was not subjected to the procedure of the invention.

After reaction at 37° C. for 24 hours, cells were fractionated on CD34 cell selection flasks and counted.

Luciferase activity was then assayed in the cells, with the results shown in table 1. It can be seen that luciferase activity is only detectable over background levels in CD34+ cells, demonstrating the specificity of the targeting system used.

EXAMPLE 12

Biologically Active Agents According to the Invention

A biologically active agent according to the invention includes any agent having biological activity that can be transferred into a host cell as described herein. Such agents may be any agent capable of eliciting a biological effect in a cell, for example, proteins, nucleic acids, ions or other biologically active molecules.

As described herein, the biologically active agent may be a nucleic acid comprising at least one transcription unit encoding a proteinaceous or RNA molecule capable of eliciting a biological effect. The transcription unit may encode any protein; for example, a growth factor, hormone, cytokine, a transcription factor, a cell surface protein or a structural protein of any kind. The protein may contain one or more domains of known function, or may consist of a single domain of a known protein. The protein may be homologous to the target cell or deficient, absent or mutated therein. For example, the transcription unit may encode a protein effective in the therapy of an infectious disease, for example in HIV therapy. Alternatively, the transcription unit may encode a protein capable of correcting a genetic defect or a protein deficiency.

In HIV therapy, the protein may be a non-specific toxin or an anti-viral agent whose expression or activity has been modified for anti-HIV use, for example by using an HIV-specific transactivation system to express the protein (see United Kingdom patent application no. 9305759.4).

Alternatively, the agent may be specifically designed as an anti-HIV agent. For example, a decoy gene, encoding trans-dominant negative mutants of HIV peptides such as the tat, nef, vpu, vpr or rev gene products, which have been modified such that their activating properties are abolished but they retain the ability to compete with the natural virus-encoded protein. See WO 9014427; Echetbu and Rice, 1993; Pearson et al., 1990.

Anti-viral agents known as decoys are antagonists to viral infection and/or production, either at the transcriptional or translational level. Thus, the invention encompasses agents and methods in which anti-viral decoys are nucleic acid decoys or protein decoys. In either embodiment, the decoy will either bind to a natural viral sequence or protein and thus preclude that sequence or protein from effecting its natural function in the cell, or it will take the place of the natural sequence or protein and thus act as a competitive inhibitor. Decoys and their use in anti-viral therapy are discussed in general in Infect. Control Hosp. Epidermial, 1991, 12:744 and in Anal. Chem., 1991, 83:273A.

Decoys useful according to the invention include but are not limited to the following. Transdominant mutants have been used in a number of viral systems to abolish or attenuate viral infection; for example, transdominant mutants of viral transactivators which prevent the wild type protein from transactivating a target gene. Transdominant mutants of E1A are discussed in Glen et al., 1987, Mol. Cell. Biol. 4:1004; of tax in Wachsman et al., 1987, Sci. 235:674;

and of VM65 in Friedman et al., 1988, Nature 335:452. Transdominant mutations in HIV genes are described in Platika et al., 1989, Jour. Cell. Biochem. 16:40 (TAT gene) and Berac et al., 1992, Proc. Nat. Aca. Sci. 87:9870 (REV gene). A dominant negative REV transactivator is also described in Lee et al., 1994, Jour. Viral. 88:8254. Other HIV transactivator mutants are described in Lee et al., 1992, Neu. Biol. 4:66 (RRE-derived sequences); Sullenger et al., 1991, Jour. Virol. 65:6811; (RNA decoy sequences); Lisziewicz et al., 1993, Proc. Nat. Aca. Sci. 90:8000 (TAT RNA decoy); Tanaka et al., 1994, Nucl. Acids Res. 22:3069; Yuyama et al., 1994, Nucl. Acids Res. 22:5060 (Ribozyme decoys for TAT and REV); Sullenger et al., 1990, Cell 63:601 (TAR decoy); Bahner et al., 1993, Jour. Virol. 67:3199 (transdominant negative mutants of HIV-1).

Other decoys include an interleukin-1 receptor antagonist (Evans et al., 1994, Receptor 4:9), and a type II receptor as a decoy for IL-1 (Re et al., 1994, Jour. Exp. Med. 179:739).

For the correction of a genetic defect or a protein deficiency, such a protein may be a lysosomal enzyme for the correction of Gaucher's or Auber's disease (Scott et al., 1990; Sorga et al., 1987), the a or B globin gene for the correction of sickle cell anemia or thalassaemia, or calcitonin or α1 antitrypsin to prevent the onset or progression of osteoporosis or emphysema.

Furthermore, it is envisaged that the product of the transcription unit may be an RNA molecule, such as an antisense RNA molecule (Mirabelli et al., 1991) or a ribozyme tailored to act in a specific manner (Cech et al., 1992).

Transcription units, or genes, useful according to the invention, which may be substituted for the luciferase gene as described above, are as follows.

For correction of a genetic defect or a protein deficiency, a gene encoding a lysosomal enzyme may be used to correct Gaucher's or Auber's disease; see Scott et al., 1990, Sorga et al., 1987. The α- or β-globin gene may be used to correct sickle cell anemia or thalassemia. The calcitonin or α-1 anti-trypsin gene may be used to prevent the onset or progression of osteoporosis or emphysema.

Dosage and Mode of Administration

Cells targeted for gene transfer in accordance with the invention include any cells to which the delivery of a gene is desired, for example, immune cells such as T-cells, B-cells, macrophages, hematopoietic cells, and dendritic cells. Cells or cell populations can be treated in accordance with the invention.

In vitro and ex vivo preparations are contemplated according to the invention. Transfected cells are administered to the patient, preferably in a biologically compatible solution or a pharmaceutically acceptable delivery vehicle, by injection, intravenously, intraperitoneally or by any number of other routes. The dosages administered will vary from patient to patient and will be determined by the level of enhancement of function of the transferred genetic material balanced against any risk or deleterious side effects. Generally, $10^6$ transferred cells are intorduced into the patient, with decreasing dosages of $10^5$, $10^4$, and $10^3$ cells administered where appropriate. Monitoring levels of transfection, gene expression and/or the presence or levels of normal encoded protein will assist in selecting and adjusting the dosages administered.

Cell populations with defective genes can be removed from the patient or otherwise provided, transduced with a normal gene in accordance with the invention, then reintroduced into the patient.

Other Embodiments

The invention is described above by way of example only, and numerous modifications of detail will be apparent to those skilled in the art which fall within the scope of the appended claims.

TABLE 1

| Sample | Viability total | Viability relative | Cells Recovered CD34+ | Cells Recovered CD34 | Luciferase Activity L.U./mg CD34+ | Luciferase Activity L.U./mg CD34 | Electric Shock | Fusogenic Peptide |
|---|---|---|---|---|---|---|---|---|
| A | 70% | 83.3% | $6.3 \times 10^5$ | $1.35 \times 10^7$ | 1457 | 1800 | + | − |
| B | 60% | 71.4% | $5.6 \times 10^5$ | $1.20 \times 10^7$ | 2800 | 1500 | + | − |
| C | 52% | 61.9% | $4.8 \times 10^5$ | $1.00 \times 10^7$ | 4428 | 1642 | + | − |
| D | 84% | 100% | $4.9 \times 10^5$ | $1.15 \times 10^7$ | 1814 | 1756 | − | − |

References

Bonifer et a&., (1990), EMBO J., 9, 2843–2848

Cech et al., (1992), J. Biol. Chem., 267, 17479–17482

Daniels at al., (1987), EMBO J., 6, 1459–1465

Demuynck et al., (1992), Eur. J. Cancer, 28, 381–386

Echetbu and Rice, (1993), J. Aquis. Immune Defic. Syndr., 6, 550–557

Hirsch et al., (1993), Transplant Proceedings 21, 138–139

Mirabelli et al., (1991), Anticancer Drug Des., 6, 647–661

Mouneimne et al., (1989), BBRC, 159, 34–40

Pearson et al., (1990), PNAS, 87, 5079–5083

Powell et al., (1989), Biophys. J., 56, 1163–1171

Roux et al., (1989), PNAS, 86, 9079

Scott et al., (1990), PNAS, 11, 9695

Sorga et al., (1987), PNAS, 84, 906–904

Titomirov at al., (1991), BBA, 1088, 131–134

Trubetskoy et al., (1992), Bioconjugate Chem., 3, 323–327

Tsong, (1991), Biophys. J., 60, 297–306

Wagner at al., (1990), PNAS, 87, 3410–3414

Wagner et al., (1991), PNAS, 89, 7934–7938

Weaver, (1993), J. Cel. Biochem., 51, 426–435

White, (1990), Ann. Rev. Physiol., 52, 675–697

Wiley and Skehel, (1987), Ann. Rev. Biochem., 5, 365–394

Wilson et al., (1981), Nature, 38, 373–378

Wong and Huang, (1987), PNAS, 84, 7851

Wu et al., J. Biol. Chem., (1989), 264, 16985–16987

Wu and Wu, J. Biol. Chem., (1987), 262, 4429–4432

We claim:

1. An in vitro method for delivering to a target cell in a population of cells a nucleic acid molecule, the method comprising the steps of:
   a) exposing the population of cells to a complex comprising the nucleic acid molecule and a ligand which binds to the target cell; and
   b) subjecting the population of cells to a mild electric field.

2. The method of claim 1 wherein the complex comprises an endosomal disruption agent.

3. The method of claim 2 wherein the endosomal disruption agent is an influenza virus haemagglutinin fusogenic peptide.

4. The method of claim 1 wherein the population of cells is heterogenous.

5. The method of claim 1 wherein the target cell is a cell of a subpopulation of said population of cells.

6. The method of claim 1 wherein the nucleic acid molecule encodes a protein or ribozyme.

7. The method of claim 1 wherein the nucleic acid molecule is a gene useful in therapy.

8. The method of claim 7 wherein the gene is useful in the correction of a genetic defect.

9. The method of claim 7 wherein the gene is useful in the therapy of an infectious disease.

10. The method of claim 9 wherein the infectious disease is AIDS.

11. The method of claim 10 wherein the nucleic acid molecule encodes a decoy protein or ribozyme.

12. The method of claim 7 wherein the gene is useful in the correction of a protein deficiency.

13. The method of claim 1 wherein the ligand is an antibody or a fragment thereof.

14. The method of claim 1 wherein the ligand is a growth factor.

15. The method of claim 1 wherein the target cell is a stem cell.

16. The method of claim 15 wherein the target cell is a haematopoietic stem cell.

17. The method of claim 1 wherein the target cell found in a population of hematopoietic stem cells.

18. The method of claim 17 wherein the target cell is a T cell.

19. An in vitro method of transporting across a cell membrane a biologically active agent, the method comprising
   a) exposing the cell membrane of an intact cell in vitro to a complex comprising a nucleic acid and a ligand which binds to the target cell; and
   b) subjecting the cell membrane in vitro to a mild electric field.

* * * * *